United States Patent
LaVay et al.

(10) Patent No.: US 7,157,105 B1
(45) Date of Patent: Jan. 2, 2007

(54) CRANBERRY ALKOXY ESTERS AS A DELIVERY SYSTEM FOR NATURAL ANTIOXIDANTS

(75) Inventors: Carter LaVay, Riverside, CT (US); Anthony J. O'Lenick, Jr., Dacula, GA (US)

(73) Assignee: Zenitech LLC, Old Greenwich, CT (US)

( * ) Notice: Subject to any disclaimer, the term of this patent is extended or adjusted under 35 U.S.C. 154(b) by 517 days.

(21) Appl. No.: 10/620,899

(22) Filed: Jul. 17, 2003

(51) Int. Cl.
*A01N 65/00* (2006.01)

(52) U.S. Cl. ...................................... 424/725

(58) Field of Classification Search ..................... None
See application file for complete search history.

(56) References Cited

U.S. PATENT DOCUMENTS 6,391,345 B1    5/2002    Heeg et al.

*Primary Examiner*—Michael Meller

(57) ABSTRACT

The present invention relates to cranberry seed oil derivatives derived by the reaction of polyoxyalkylene glycol compounds and cold pressed cranberry seed oil. The choice of cold pressed cranberry seed oil as a raw material in the preparation of the compounds of the present invention is critical, since it has been found that the cold pressed cranberry seed oil contains antioxidants, antimicrobial compounds and which when reacted with a polyoxyalkylene glycol compounds, result in products that deliver said actives to the skin and hair, resulting in protection of the skin and hair from environmental factors such as acid rain, ozone attack and UV degradation.

19 Claims, No Drawings

CRANBERRY ALKOXY ESTERS AS A DELIVERY SYSTEM FOR NATURAL ANTIOXIDANTS

BACKGROUND OF THE INVENTION

The present invention relates to cranberry seed oil derivatives derived by the reaction of polyoxyalkylene glycol and cold pressed cranberry seed oil. The choice of cold pressed cranberry seed oil as a raw material in the preparation of the compounds of the present invention is critical, since it has been found that the cold pressed cranberry seed oil contains a unique antioxidant which when reacted with polyoxyalkylene glycol resulting in products that deliver said actives to the skin and hair, resulting in protection of the skin and hair from environmental factors such as acid rain, ozone attack and UV degradation.

U.S. Pat. No. 6,391,345 issued May 2002 describes the refining of cold pressed cranberry seed oil, and is incorporated herein by reference. American cranberries, *Vaccinium macrocarpon*, are native plants of open, acid peat bogs in North America. Cranberry plants are evergreen perennial vines that produce runners and upright branches with terminal flower buds.

Cranberries have historically been harvested and either ingested as whole berries, such as in cranberry sauce, or have been processed for their juice. Pulp remaining after cranberry juice extraction processing has historically been regarded as an undesirable waste product with little or no utility.

In the United States, cranberries are grown and are harvested in the Northeast, Northwest and Great Lakes regions. Cranberries ripen and are harvested in autumn, which has made cranberries a holiday food. Cranberries have not changed significantly in appearance and nutritional value over time. Cranberries have typically been stored by freezing or drying the whole berries.

Cranberries have become a popular food only in recent years because cranberries have a very bitter taste. Historically, processors have not dealt well with the taste. Cranberries are known to contain quininic acid. It is the quininic acid that imparts to cranberries, the bitter taste. Cranberry juice has become more palatable because it is blended with other sugar-containing aqueous liquids.

Apart from an undesirable taste, quininic acid is believed to have nutraceutical properties. When ingested, quininic acid is converted to hippuric acid. Hippuric acid is believed to remove toxins from the bladder, kidneys, prostate and testicles. Under normal circumstances, oils useful in the cosmetic industry are refined with a variety of steps that are designed to maximize triglyceride content, and minimize color and odor. These steps include steam distillation, a process in which steam is sparged through the oil to remove odor and color bodies and solvent extraction with compounds like hexane, which remove additional odor and color bodies. We have learned that these processes, while improving color and odor, remove many of the desirable "active" materials like tocopherols, antioxidants and the like. What results is a light color, low odor triglyceride with no appreciable added skin benefits. We have surprisingly learned that when the cranberry seed oil that is cold processed is reacted with specific compounds, the actives (normally removed in non-cold press process) remain in the product, become water-soluble and have outstanding activity on the skin. In essence two things happen when the cold pressed cranberry seed oil is reacted with polyoxyalkylene glycols. First the triglyceride reacts giving a product which is water-soluble. Secondly, the water-soluble product solubilized the active components there as a consequence of cold pressing. Thirdly, these very desirable materials are deposited on the skin and have a proclivity to remain on the skin. The result is a unique delivery of the actives to the skin from totally natural fruit oil.

The compounds of the present invention all get their unique properties in personal care applications from the cold pressed cranberry oil which is made water soluble by reaction with polyoxyalkylene glycol compounds.

SUMMARY OF THE INVENTION

The present invention relates to a series of products derived from the reaction of cold pressed cranberry oil and various polyoxyalkylene glycol compounds.

The present invention also relates to a process of treating hair and skin, which comprises contacting the hair and skin with an effective anti-oxidant containing amount of cranberry compounds of the preset invention.

DETAILED DESCRIPTION OF THE INVENTION

U.S. Pat. No. 6,391,345 issued May 2002 describes a cold pressed process for cranberry oil. These compounds surprisingly survive the reaction with polyoxyalkylene glycol compounds, resulting in a highly substantive delivery system for these very desirable natural compounds.

Also critical to the practice of the present invention is the fatty composition of the cold pressed Cranberry oil. This Cranberry oil has a substantially clear appearance with a pale yellow color.

Cold Pressed Cranberry Oil is a triglyceride conforming to the following structure:

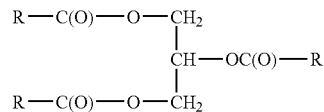

The R—C(O)— group has the following composition:

| Component | % Weight |
| --- | --- |
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic(alpha) | 30 to 35 |
| 20:0 arachidic | 0.13 |
| 20:1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 eicosatrienoic | 0.01 |
| Eicosapentaenoic | 0.01 |
| Behenic | 0.03 |
| Erucic | 0.02 |

-continued

| Component | % Weight |
| --- | --- |
| Docosapentaenoic | 0.01 |
| Tricosanoic | 0.01 |
| Lignoceric | 0.02 |
| Nervonic | 0.02 |

The oil also contains the following very critical "active" components for skin and hair care:

| Compound | mg/kg |
| --- | --- |
| Campesterol/brassicasterol (mg/kg) | 66.0 |
| Stigmasterol (mg/kg) | 68.0 |
| Beta-sitosterol (mg/kg) | 1319.0 |
| Phosphatidylinositiol (mg/kg) | 9.9 |
| Phosphatidyicholine (mg/kg) | 202.0 |
| Alpha-tocopherol (mg/kg) | 341.0 |
| Gamma-tocopherol (mg/kg) | 110.0 |

When the oil is exposed to steam strip and solvent extraction the concentration of the "active" components drops to vanishingly small levels and the activity is lost.

As can be seen, the cold pressed cranberry seed oil is a rich source of compounds having important properties when applied to hair and skin. Stigmasterol is an anti-stiffness factor. Beta-sitosterol has use as an antihyperlipoproteinemic agent. One or more of the campesterol, stigmasterol and beta-sitosterol has inflammatory activity and may be useful in the treatment of gingivitis, rash, eczema, and other skin lesions. It is also believed that these compounds found in cranberry seed oil have activity as sunscreen agents. Since some of the compounds present in cranberry oil have absorbance in the UV-B range. It is this range that causes the greatest cellular damage. The cold pressed cranberry oil can shield against UV-A induced damage by scattering light as well as by light spectrum absorption. The cold pressed cranberry oil has, then activity as a broad spectrum UV protectant. The cranberry oil may be used alone or in combination with other conventional sunscreens.

The phosphatidylinositiol and phosphatidylcholine and tocopherols are highly desirable materials used on skin. The phosphatidylcholine, also known as lecithin, is found in human beings in the nervous system and the brain. Lecithin also has use as an edible and digestible surfactant. It is usable in manufacturing foods such as margarine and chocolate. Lecithin is a natural antioxidant that can increase oil stability and shelf life. Lecithin also has use in pharmaceuticals, cosmetics, skin care, and in treating leather and textiles.

Cold pressed cranberry seed oil has a very high concentration of gamma tocopherol. This level is much higher than is found in oils such as safflower and grape, which are 11 and 33, respectively. The gamma tocopherol has the most antioxidant capacity of all of the tocopherols and contributes to the stability of highly unsaturated oils in the cranberry oil. It is believed that the presence of the high gamma tocopherol concentration makes cranberry oil an excellent additive to animal food-both human and non-human. The gamma tocopherol may be as important as alpha tocopherol in preventing degenerative diseases.

Cold pressed cranberry seed oil has a high linolenic acid content. Linolenic acid has been implicated as a food additive and nutraceutical in preventing coronary heart disease and cancer. Cranberry oil also has a high polyunsaturated: saturated ratio in a neutral lipid fraction, of 10:1. This ratio is regarded as having value in reducing serum cholesterol, atherosclerosis and in preventing heart disease.

Cold pressed cranberry seed oil has a rather dark yellow to orange color because it contains carotenoids. The carotenoids are usable as colorant substitutes for materials such as carotenes, annotos, and apocarotenals used in the nutraceutical and oil industries.

The cold pressed cranberry seed oil, containing all of the above desirable compounds, is reacted with a polyoxyalkylene glycol conforming to the following structure:

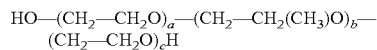

wherein a, b and c are independently integers ranging from 0 to 40, with the proviso that a+b+c equal at least 5.

To provide a composition conforming to the following structure:

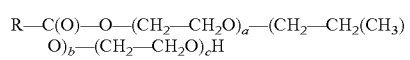

and

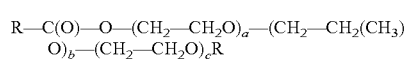

wherein;

R is derived from cold pressed cranberry seed oil and has the composition;

| Component | % by Weight of "R" |
| --- | --- |
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |
| 20:1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 eicosatrienoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02 |

Also present in the product are the following "actives"

Compound

Campesterol/brassicasterol

Stigmasterol

Beta-sitostero

Phosphatidyl inositiol

Phosphatidylcholine

Alpha-tocopherol

Gamma-tocopherol

The reaction is a mixture of mono and di ester and is a consequence of the reaction process. Using an excess of cranberry oil results in more di-ester, but also results in a water insoluble oil that comes out of aqueous system.

The current invention describes a composition, which is prepared by the reaction of:

(1) cold pressed cranberry seed oil and (2) polyoxyalkylene glycol confirming to the following structure;

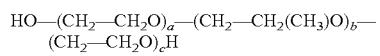

wherein a, b and c are independently integers ranging from 0 to 40, with the proviso that a+b+c equal at least 5.

The compounds of the present invention deliver these active products to skin, therefore the invention also discloses a process for conditioning skin which comprises contacting the skin with an effective conditioning concentration of a cranberry polyoxyalkylene ester composition, which conforms to the following structure;

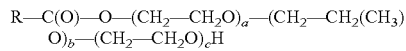

and

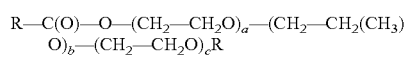

wherein;

R is derived from cold pressed cranberry seed oil and has the following composition:

| Component | % by Weight of "R" |
|---|---|
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |
| 20:1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 eicosatrienoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02 |

Also present in the product are the following "actives"

Compound

Campesterol/brassicasterol

Stigmasterol

Beta-sitostero

Phosphatidylinositiol

Phosphatidylcholine

Alpha-tocopherol

Gamma-tocopherol and a, b and c are independently integers ranging from 0 to 40, with the proviso that a+b+c equal at least 5.

Preferred Embodiments

In a preferred embodiment a is 5, b is 0, and c is 0.
In a preferred embodiment a is 5, b is 5, and c is 5.
In a preferred embodiment a is 0, b is 10, and c is 0.
In a preferred embodiment a is 10, b is 10, and c is 0.
In a preferred embodiment a is 20, b is 5, and c is 20.
In a preferred embodiment a is 1, b is 10, and c is 5.
In a preferred embodiment a is 40, b is 40, and c is 40.
In a preferred embodiment a is 10, b is 10, and c is 15.

EXAMPLES

The compounds of the present invention are made from commercially available raw materials.

Raw Materials

Cold Pressed Cranberry Seed Oil

Cold Presses Cranberry seed oil is an item of commerce sold by Regal Trade & Consult LLC. of Hoboken, N.J. It is processed using U.S. Pat. No. 6,391,345 issued May 2002, only applied to Cranberry seed oil not cranberry seed oil.

Polyoxyalkylene Glycol

Polyoxyalkylene glycol compounds are items of commerce and arte available from a variety of sources including Siltech Corporation Toronto Ontario Canada. The structures presented were determined by NMR and are not dependant upon trade names.

| Example | a | b | c |
|---|---|---|---|
| 1 | 5 | 0 | 0 |
| 2 | 5 | 5 | 5 |
| 3 | 0 | 10 | 0 |
| 4 | 10 | 10 | 0 |
| 5 | 20 | 5 | 20 |
| 6 | 1 | 10 | 5 |
| 7 | 40 | 40 | 40 |
| 8 | 10 | 10 | 15 |

General Procedure

To grams of 400 grams of Cold Pressed Cranberry seed oil is added. The specified number of grams of polyoxyalkylene glycol (example 1–8). The reaction mass is heated to 180–200° C., under good agitation. As the reaction mass is held at temperature, the material clears and becomes homogeneous. The reaction mass is held for eight hours to 12 hours at reaction temperature. The reaction progress if followed by hydroxyl value and % ester. The resulting product is used without additional purification.

| | Polyoxyalkylene Glycol | |
|---|---|---|
| Example | Example | Grams |
| 9 | 1 | 111.0 |
| 10 | 2 | 368.5 |
| 11 | 3 | 296.0 |
| 12 | 4 | 516.0 |
| 13 | 5 | 1030.0 |
| 14 | 6 | 428.0 |
| 15 | 7 | 2806.0 |
| 16 | 8 | 846.0 |
| 17 | 1 | 222.0 |
| 18 | 2 | 737.0 |
| 19 | 3 | 592.0 |
| 20 | 4 | 1032.0 |
| 21 | 5 | 2059.0 |
| 22 | 6 | 856.0 |
| 23 | 7 | 5612.0 |
| 24 | 8 | 1692.0 |

APPLICATIONS EXAMPLES

The compound of the present invention are water-soluble or water dispersible surface active compound that has an extraordinary skin feel and provide antioxidant, and other desirable properties from the components that are not removed from the cranberry oil when it is cold processed. The cold processing leaves behind the desirable components, which in turn are not destroyed by the reaction and surprisingly, become oil-soluble and delivered to the skin. In addition, materials are emulsifiers, and can be blended with dimethicone copolyol compounds to improve deposition on the skin.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A cranberry polyoxyalkylene glycol ester composition conforming to the following structure:

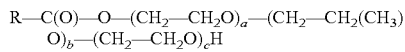

and

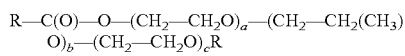

wherein;
R is derived from cold pressed cranberry seed oil;
a, b and c are independently integers ranging from 0 to 40, with the proviso that a+b+c equal at least 5
wherein the R—C(O)— group has the following composition:

| Component | % Weight |
|---|---|
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |
| 20:1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 eicosatrienoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02. |

2. A composition of claim 1 wherein a is 5, b is 0, and c is 0.

3. A composition of claim 1 wherein a is 5, b is 5, and c is 5.

4. A composition of claim 1 wherein a is 0, b is 10, and c is 0.

5. A composition of claim 1 wherein a is 10, b is 10, and c is 0.

6. A composition of claim 1 wherein a is 20, b is 5, and c is 20.

7. A composition of claim 1 wherein a is 1, b is 10, and c is 5.

8. A composition of claim 1 wherein a is 40, b is 40, and c is 40.

9. A composition of claim 1 wherein a is 10, b is 10, and c is 15.

10. A process for treating hair and skin with an effective antioxidant concentration of a cranberry polyoxyalkylene glycol ester composition conforming to the following structure:

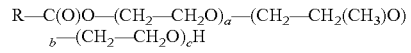

and

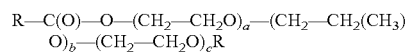

wherein;
R is derived from cold pressed cranberry seed oil;
a, b and c are independently integers ranging from 0 to 40, with the proviso that a+b+c equal at least 5
wherein the R—C(O)— group has the following composition:

| Component | % Weight |
|---|---|
| 16:0 palmitic | 5.0 to 6.0 |
| 18:0 stearic | 1.0 to 2.0 |

-continued

| Component | % Weight |
|---|---|
| 18:1 oleic | 20 to 25 |
| 18:2 linoleic | 35 to 40 |
| 18:3 linolenic (alpha) | 30 to 35 |
| 20:0 arachidic | 0.13 |
| 20:1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 eicosatrienoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02. |

11. A process of claim 10, wherein said effective antioxidant concentration ranges from 0.1% to 10.0% by weight.

12. A process of claim 11 wherein a is 5, b is 0, and c is 0.

13. A process of claim 11 wherein a is 5, b is 5, and c is 5.

14. A process of claim 11 wherein a is 0, b is 10, and c is 0.

15. A process of claim 11 wherein a is 10, b is 10, and c is 0.

16. A process of claim 11 wherein a is 20, b is 5, and c is 20.

17. A process of claim 11 wherein a is 1, b is 10, and c is 5.

18. A composition of claim 11 wherein a is 40, b is 40, and c is 40.

19. A process of claim 11 wherein a is 10, b is 10, and c is 15.

\* \* \* \* \*